US00PP29477P2

(12) United States Plant Patent
Yanny

(10) Patent No.: US PP29,477 P2
(45) Date of Patent: Jul. 10, 2018

(54) ***SYRINGA* PLANT NAMED 'PINK FLOWER SELECT'**

(50) Latin Name: *Syringa patula*
Varietal Denomination: Pink Flower Select

(71) Applicant: JN Plant Selections, LLC, Milwaukee, WI (US)

(72) Inventor: Michael D. Yanny, Milwaukee, WI (US)

(73) Assignee: JN PLANT SELECTIONS, LLC, Milwaukee, WI (US)

( * ) Notice: Subject to any disclaimer, the term of this patent is extended or adjusted under 35 U.S.C. 154(b) by 19 days.

(21) Appl. No.: 15/530,155

(22) Filed: Dec. 7, 2016

(51) Int. Cl.
*A01H 5/00* (2018.01)

(52) U.S. Cl.
USPC ..... Plt./248
CPC ..... *A01H 5/00* (2013.01)

(58) Field of Classification Search
USPC ..... Plt./248
CPC ..... A01H 5/00
See application file for complete search history.

*Primary Examiner* — Kent L Bell
(74) *Attorney, Agent, or Firm* — Penny J. Aguirre

(57) ABSTRACT

A new cultivar of *Syringa patula* plant named 'Pink Flower Select' that is characterized by its floriferous blooming habit with inflorescences covering the top two-thirds of the plant when in full bloom, its large inflorescences that are pale pink to white in color that open from pink buds, its fall foliage that is red-purple with yellow-green margins and veins in the fall in most years in Southern Wisconsin, its ability to be readily rooted from softwood stem cuttings, its ability to be readily overwintered (even as young plants) with cold hardiness to at least U.S.D.A. Zone 3b, and its resistance to root rot) and powdery mildew.

2 Drawing Sheets

Botanical classification: *Syringa patula.*
Variety denomination: 'Pink Flower Select'.

BACKGROUND OF THE INVENTION

The present invention relates to a new and distinct cultivar of *Syringa patula* and will be referred to hereafter by its cultivar name, 'Pink Flower Select'. 'Pink Flower Select' is a new cultivar of lilac grown for use as a landscape and ornamental plant.

'Pink Flower Select' arose as a seedling of open pollinated plants of *Syringa patula* 'Miss Kim' (not patented) in Menomonee Falls, Wis. The Inventor selected the new cultivar as a single unique plant from amongst the seedlings of the above cross in the summer of 1999.

Asexual propagation of the new cultivar was first accomplished by the Inventor by softwood stem cuttings in June of 1999 in Menomonee Falls, Wis. Asexual propagation of the new cultivar by softwood stem cuttings has determined that the characteristics are stable and are reproduced true to type in successive generations.

SUMMARY OF THE INVENTION

The following traits have been repeatedly observed and represent the characteristics of the new cultivar. These attributes in combination distinguish 'Pink Flower Select' as a unique cultivar of *Syringa.*

1. 'Pink Flower Select' exhibits a floriferous blooming habit with inflorescences covering the top two-thirds of the plant when in full bloom.
2. 'Pink Flower Select' exhibits large inflorescences that are pale pink to white in color that open from pink buds.

3. 'Pink Flower Select' exhibits fall foliage that is red-purple with yellow-green margins and veins in the fall in most years in Southern Wisconsin.
4. 'Pink Flower Select' is readily rooted from softwood stem cuttings.
5. 'Pink Flower Select' overwinters readily even as young plants with cold hardiness to at least U.S.D.A. Zone 3b.
6. 'Pink Flower Select' exhibits good resistance to root rot and powdery mildew.

The female parent of 'Pink Flower Select', 'Miss Kim', differs from 'Pink Flower Select' in being less floriferous, in having smaller inflorescences that are more lavender in color, and in commencing bloom later. The new *Syringa* can be most closely compared to the *Syringa* cultivars 'KLMone' (not patented) and 'Bailbelle' (U.S. Plant Pat. No. 12,294). 'KLMone' is similar to 'Pink Flower Select' in having flowers that are light pink in color and in having a plant habit that is round in shape. 'KLMone' differs from 'Pink Flower Select' in having a less floriferous bloom habit. 'Bailbelle' is similar to 'Pink Flower Select' in having pink flowers. 'Bailbelle' differs from 'Pink Flower Select' in having flowers that are darker pink in color, in having a less floriferous bloom habit, and in being more susceptible to root rot.

BRIEF DESCRIPTION OF THE DRAWINGS

The accompanying colored photographs illustrate the overall appearance and distinct characteristics of the new *Syringa*. The photographs were taken of a 10 year-old plant as grown outdoors in a nursery in Menomonee Falls, Wis.

The photograph in FIG. 1 provides a side view of a plant of 'Pink Flower Select' in bloom.

Figure 1:
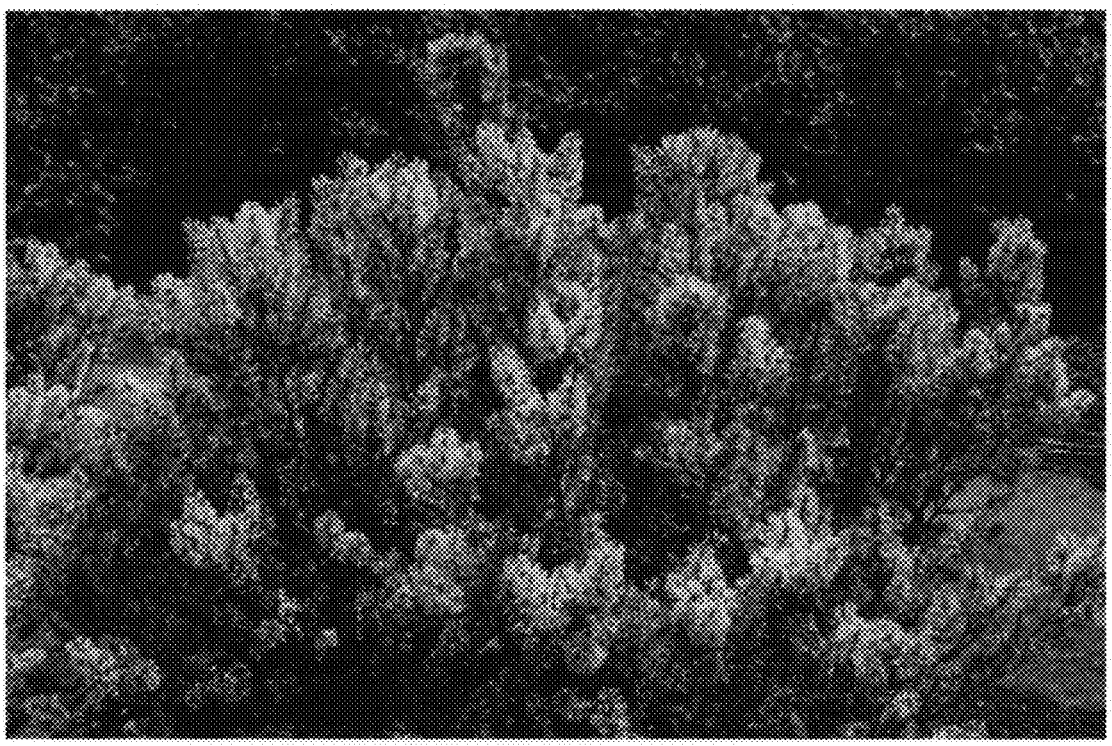
Figure 2:
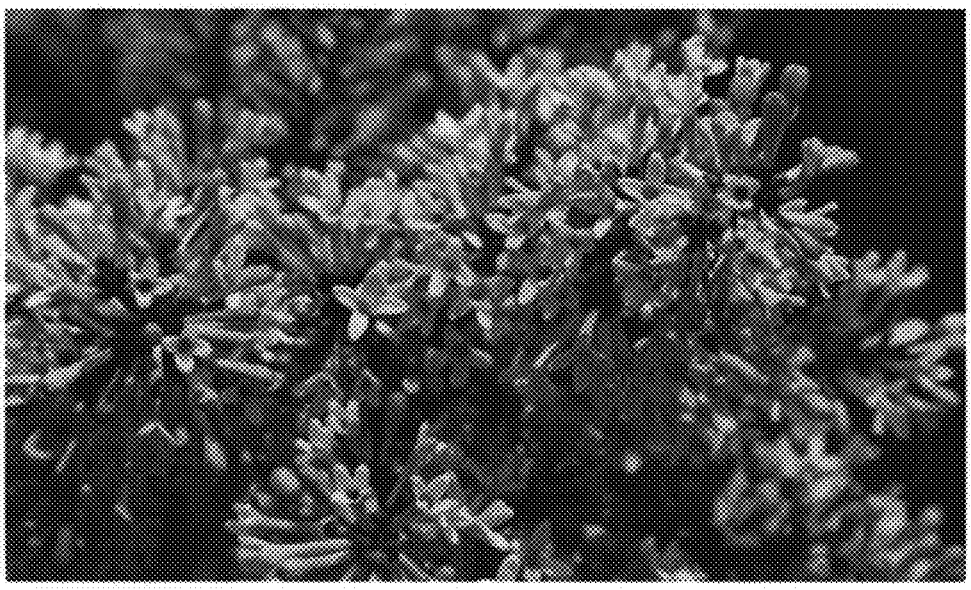

The photograph in FIG. 2 provides a close-up view of the inflorescences of 'Pink Flower Select'.

Figure 3:
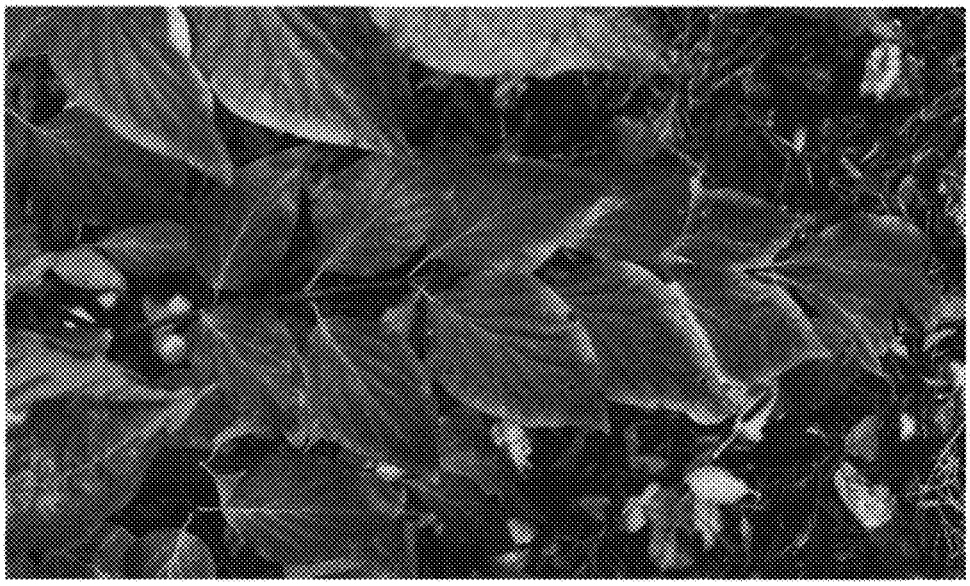

The photograph in FIG. 3 provides a close-up view of the fall foliage of 'Pink Flower Select'.

The colors in the photographs are as close as possible with the photographic and printing technology utilized and the color values cited in the detailed botanical description accurately describe the colors of the new *Syringa*.

DETAILED BOTANICAL DESCRIPTION

The following is a description of 3 year-old plants as grown outdoors in two-gallon containers in Menomonee Falls, Wis. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period*.—Two to three weeks in late May to early June in southern Wisconsin.

*Plant type*.—Deciduous shrub.

*Plant habit*.—Compact, upright and rounded.

*Height and spread*.—An average of 1.5 m in height and width as a 10 year-old plant grown in the landscape.

*Hardiness*.—At least in U.S.D.A. Zones 3b to 7a, even as young plants.

*Diseases*.—Good resistance to powdery mildew (*Microsphaera penicullata*) and root rot (*Phytophthora* spp) has been observed.

*Root description*.—Fibrous and dense, a blend of 158A and 161A in color.

*Propagation*.—Softwood stem cuttings.

*Growth rate*.—Moderate.

*Root development*.—Softwood cuttings root readily in 6 to 8 weeks in a hot house under intermittent mist, rooted cuttings are easily overwintered and roots will fully develop in a one-quart container by mid-summer the following year.

Branch description:

*Branch shape*.—Rounded.

*Branch color*.—One year-old and 2 year-old wood; a blend of 198A and 198B.

*Branch size*.—An average of 65 cm in length and 5 mm in width.

*Branch surface*.—One year-old wood; slightly rugose, dull and bark-like, moderately covered with lenticels, an average of 15 lenticels per cubic cm, NN155A in color and an average of 1 mm in diameter, two year-old wood; glabrous, dull and bark-like, moderately covered with lenticels, an average of 26 lenticels per cubic cm, 159A in color and average of 1 mm in diameter.

*Internode length*.—An average of 5 cm.

*Branching*.—Branches held at multiple angles ranging between 60° and 90° (90°=straight upright).

Foliage description:

*Two flushes of foliage*.—1$^{st}$ flush (early spring) and 2$^{nd}$ flush of foliage (late spring) with any differences noted.

*Leaf shape*.—Ovate to lanceolate.

*Leaf division*.—Simple.

*Leaf base*.—Cuneate.

*Leaf apex*.—Acuminate.

*Leaf fragrance*.—None.

*Leaf venation*.—Pinnate, upper surface color; closest to N144A and slighty transluscent on young leaves, lower surface matches leaf color and slighty transluscent on young leaves; color changes to 151A to 151B in the fall.

*Leaf margins*.—Entire and slightly undulate.

*Leaf arrangement*.—Opposite, pseudoverticillate.

*Leaf attachment*.—Petiolate.

*Leaf surface*.—Both surfaces are dull and glabrous.

*Leaf size*.—An average of 7 cm in length and 4.4 cm in width in early spring (first flush) and an average of 5 cm in length and 2.4 cm in width in late spring (2$^{nd}$ flush).

*Leaf quantity*.—An average of 120 leaves per branch 15 cm in length.

*Leaf color*.—Young leaves upper and lower surface; 144A to 144B, mature leaves upper and lower surface; 147A to 147C; color changes to 187A to 187B (darkest with most sun exposure) with margins and veins 151A to 151B in the fall.

*Petioles*.—First flush; An average of 1.3 mm in length and 1 mm in width, 2$^{nd}$ flush; an average of 7 mm in length and 1 mm in width, color matches leaf coloration, surfaces glabrous.

*Bracts*.—An average of 2, at the base of a leaf cluster, an average of 5 mm in length and 4 mm in width, upper and lower surfaces; dull and glabrous and 144B in color.

Inflorescence description:

*Inflorescence type*.—Thyrse compound panicles on terminals and laterals of previous years' growth, ovate in overall shape.

*Inflorescence size*.—An average of 20 cm in length and 12.7 cm in width, can reach up to 28 cm in length and 23 cm in width on vigourous young plants.

*Rachis*.—Rounded in shape, up to 18 cm in length and an average of 2 mm in width, 147B in color with lenticels <0.5 mm in length and 165D in color, surface is glabrous, strong.

*Peduncles*.—An average of 4 cm in length and 1 mm in width, 147B in color, glabrous surface, moderate strength.

*Flower buds*.—Spatulate in shape, an average of 12.5 mm in depth and 2.25 mm diameter at the apex tapering to 1 mm at the base, 65A to 65D in color with sepal portion 65C to 65D.

*Flower fragrance*.—Sweet lilac scent.

*Persistence of flowers*.—Self-cleaning, calyx persistent.

*Lastingness of flowers*.—Individual panicles bloom for about 2 weeks, depending on temperature.

*Flower quantity*.—An average of 370 flowers per compound panicle.

*Flower type*.—Salverform with spreading petals.

*Flower aspect*.—Upwards and outward.

*Flower size*.—An average of 6.5 mm in diameter and 11.5 mm in depth.

*Petals*.—4, an average of 3 mm in length and 1.5 mm in width, lower 80% fused forming a narrow tube, entire margin, acute apex, upper and lower surfaces smooth and glabrous, color; upper and lower surfaces a blend between 65C to 65D and N155B.

*Calyx.*—Campanulate, about 1.5 mm in depth and 1 mm in width, comprised of 4 fused sepals with tips unfused with acute apices, glabrous surface, 139C in color.

Reproductive organs:

*Pistils.*—1, inserted deep into calyx, average of 5 mm in length, stigma; minute in size, oval in shape, 150D in color, style; 155A in color.

*Stamens.*—2, extend beyond corolla, anthers; an average of 1 mm in length and 186B in color, filaments; about 2 mm in length, pollen; abundant in quantity and 1A in color.

*Fruit and seed.*—Seed capsules have been observed on occasion but were not produced on plants available for data collection, not a heavy seed producer.

It is claimed:

1. A new and distinct cultivar of *Syringa* plant named 'Pink Flower Select' as herein illustrated and described.

* * * * *